United States Patent [19]

Simpson

[11] Patent Number: 4,971,046

[45] Date of Patent: Nov. 20, 1990

[54] SURGICAL PRESSURE PLASTER

[75] Inventor: John M. Simpson, Dorset, United Kingdom

[73] Assignee: Hazeltine Lake & Company, Bristol, England

[21] Appl. No.: 314,044

[22] Filed: Feb. 22, 1989

[30] Foreign Application Priority Data

Feb. 22, 1988 [GB] United Kingdom ............... 8804076
Sep. 7, 1988 [GB] United Kingdom ............... 8820930

[51] Int. Cl.$^5$ ............................................. A61F 13/00
[52] U.S. Cl. ....................................... 128/155; 128/156
[58] Field of Search ........................... 128/155, 156, 157

[56] References Cited

U.S. PATENT DOCUMENTS

| | | | |
|---|---|---|---|
| 2,858,830 | 11/1958 | Robins | 128/156 |
| 3,490,448 | 1/1970 | Grubb | 128/157 X |
| 4,176,664 | 12/1979 | Kalish | 128/156 |
| 4,377,159 | 3/1983 | Hansen | 128/155 |
| 4,832,009 | 5/1989 | Dillon | 128/156 |

Primary Examiner—Alan W. Cannon
Assistant Examiner—N. Paul
Attorney, Agent, or Firm—Merchant, Gould, Smith, Edell, Welter & Schmidt

[57] ABSTRACT

A surgical pressure plaster has a pressure pad of readily compressible, resilient material, preferably having a trapezoidal cross-section with its non-parallel sides equal. The pressure pad is attached lengthwise and centrally to the adhesive surface of a highly elastic adhesive tape. Two removable protective strips and overlie the tacky surface of the elastic tape in end regions thereof and are of material stiff enough for them to have been inherently curved or angled into sections at right angles to sections adhering to the elastic tape. The protective strip may extend over the top surface of the pad which needs to be kept sterile through further anglings thereof. Using one hand only, digital pressure is exerted on the pressure pad's sides causing rotation of the projecting strips away from the pad whose surface is pressed onto a venepuncture wound site. The strips are removed, the tape ends, each stretched, are then applied to the skin, and the pad now maintains pressure on the wound and prevents bleeding.

19 Claims, 3 Drawing Sheets

4,971,046

SURGICAL PRESSURE PLASTER

FIELD OF THE INVENTION

This invention relates to a surgical pressure plaster.

BACKGROUND OF THE INVENTION

In medicine, veins are deliberately perforated by needles (venepuncture) for a variety of reasons and by a variety of persons who differ in their skills and the time available to attend to the wound site after the needle is withdrawn. A laboratory technician has to take blood samples from a large number of patients on a routine basis; an anaesthetist has to continue anaesthesia after giving a sleep-inducing injection. Both may have little time available to ensure pressure is maintained on the venepuncture site.

If pressure is not applied and blood is permitted to leak from a venepuncture site the area may become painful, bruised and therefore unsightly, or swollen due to a mass of solid blood (haematoma) forming. There may be dangerous blood volume loss in small patients. Pressure on and thrombosis of the vein can occur, rendering the vessel unusable, and this can be dangerous in life-threatening situations. When patients are being treated with anti-clotting agents, even greater care must be taken to exert pressure and ensure that bleeding does not occur.

In present practice there are at least eight varying ways of attempting to prevent bleeding following venepuncture. This indicates that none is totally satisfactory. Most utilise the attendant's time and are therefore inefficient. Some do not attempt to maintain pressure whilst some that do fail. Some dressings are clumsy in their construction. Some require the assistance of the patient or another attendant to be effective. Many are expensive to manufacture.

In general, a medical attendant should hold in one hand either the needle itself or a syringe to which the needle is attached prior to removal of the same. At this time the attendant needs to be able with the other hand to pick up a surgical dressing on which no time has been spent in prior preparation, and apply it immediately in an aseptic state directly and under pressure over the venepuncture site. This having been accomplished the needle is removed and within a few seconds the dressing must be fixed so that, without any external agency, it maintains firm pressure on the wound and prevents bleeding.

In greater detail, what is required in an aseptic surgical pressure dressing is the following:

1. It should be simple in both structure and application so that its manner of use is quickly understood by the thousands of medical attendants who would use it every day and so that manufacture would be no overriding problem.

2. Speed of application should be permitted by its simplicity of design, to permit effective blood sampling.

3. The dressing should be pressure effective, until complete haemostasis is achieved which occasionally may require that the dressing should remain not only effective in situ for 30 minutes or longer but also remain effective:

(i) at all possible anatomical venepuncture sites, e.g. the bend at the elbow (the cubital fossa) which presents a valley of varying depth; the pressure exerted must be effective on the floor of this area.

(ii) with all age groups, including those elderly patients whose subcutaneous tissues are occasionally very lax and induce a certain loss in tension in tapes after they have been pulled over central pads.

(iii) on a wide variety of sizes of puncture wound left by the needles of widely varying size which have penetrated the skin at an angle to the skin surface.

4. It should be possible to apply the dressing without the need for assistance either from the patient or another attendant. It should therefore be capable of being effectively employed in all hospital treatment areas without affecting hospital operating efficiency deleteriously.

5. The dressing should be absorbent. Effective pad pressure will prevent blood loss from the venepuncture wound but on removal of the needle a thin bloody tail is often left where the needle passes between pad and skin. Aesthetically, this blood is preferably absorbed into the dressing pad.

6. The size of the dressing should be similar to that of standard plasters, e.g. "Band-aids" (Registered Trade Mark). This is for aesthetic and comfort reasons.

7. The dressing should be non-allergenic so as not to cause local and/or generalised skin irritant rashes of true allergic character.

DESCRIPTION OF THE RELATED ART

Various proposals have already been made for creating an effective surgical pressure dressing. One was my own EP-A-0067622 which, however, fails to meet all the requirements stated above. Another, US-A-3490448 (Grubb) suffers from the need for prior preparation before pressure is applied and from failure occasionally to apply pressure directly over the puncture site, as the dressing must usually be applied in part to the skin before venepuncture is attempted, it must fail often to maintain pressure because the "slightly elastic" nature of the backing will be inadequate to counteract the mobility of the subcutaneous tissues. Finally GB-A-8600331 also requires prior preparation, and must occasionally fail to exert pressure directly over the puncture site because prior application before venepuncture is sometimes combined with the need to move the pad in a lateral direction over an undetermined distance. Also, the relatively thin pad will not reach all possible venepuncture sites, e.g. the depths of some cubital fossae. The dressing is also of complicated construction.

OBJECT OF THE INVENTION

It is thus an object of the invention both to prevent leakage of blood from the puncture hole left in a vein when a needle is removed from that vessel and to accomplish this in a quick, simple and effective manner.

SUMMARY OF THE INVENTION

According to the present invention, there is provided a surgical plaster comprising:

an elastic tape one surface of which is tacky;

a resilient sterile pressure pad attached to the tacky surface of the elastic tape in a central region thereof;

a pair of removable protective strips adhering at first sections to respective end regions of the tacky surface of the elastic tape and extending up to regions of said pad extending transversely of the tape, the strips each being of material stiff enough to ensure an inherent set curvature or angling of its form into a second section at an angle to said first section overlying the tape, said second sections being of a sufficient length to act as a support for the first section and thereby ensure that said tape is maintained in a substantially flat configuration when held adhesive tape uppermost; and means covering and maintaining sterile the surface of the pad opposite that lying on the tape prior to removal of said strips from the tape; the resilience of said pad being such that manual compression of the pad at surfaces extending lengthwise of the tape deforms the pad to an extent sufficient to alter said curvature or angling of the strips and rotate said second sections so as to increase the angles between them and the regions of the pad extending transversely of the tape.

Many variants of the present invention enabling the above object to be achieved are possible to varying degrees of efficiency by varying the shape of the resilient sterile pressure pad, the form and/or angling of the protective strips and possibly the means covering the surface of the pad opposite that lying on the tape prior to removal of the strips from the end of the resilient sterile pressure pad. However, common to all such forms of surgical plaster is the requirement that deformation of the pad should result in rotation of the second sections of the protective strips into an orientation in which they can be readily gripped to enable the protective strips to be pulled off the elastic tape immediately after applying the pressure pad to a puncture hole and prior to pressing the tape onto the skin to hold the pressure pad over the puncture hole. As a result of maintenance of sterility of the surface of the pad opposite that lying on the tape prior to removal of said strips from the ends of the pad and the application of the plaster in such manner, there is maintained sterility of all surfaces of the plaster brought into contact with the patient.

The pressure pad itself may be of any one of a variety of forms. Generally, it will be elongate and in one form of plaster embodying the invention is a rectangular block of resilient material. However, for reasons which will be detailed hereinafter, it is preferred that the pressure pad be of trapezoidal transverse cross-section with its non-parallel sides being equal and extending lengthwise of the tape, the surface lying on the tape being larger than the opposite surface.

In preferred practice, the protective strips themselves cover and maintain sterility of the surface of the pad opposite that lying on the tape prior to removal of the strips from the tape. For this purpose the protective strips adhering to the end regions of the tacky surface of the elastic tape extend up to the ends of the pad which in this case are planar surfaces extending transversely of the tape, the strips extending over the pad surface opposite that lying on the tape. The stiffness of the material of strips is sufficient to ensure an inherent set curvature or angling of its form into a section perpendicular to both that section overlying the tape and that section overlying the pad, the section of one strip lying over the pad surface opposite to that lying on the elastic tape overlapping the section of the other strip lying over such an opposite pad surface.

It is not, however, essential that the protective strips be of such length provided that the plasters be housed in sterile containers prior to use. Provided that the surface of the pad opposite that adhering to the tape lies against a sterile surface and care is taken that such opposite surface is not contacted by a medical attendant in removing the plaster from its container and applying it to a skin puncture, it suffices for the protective strips to extend only into the aforementioned second section which is at an angle to the first section which adheres to the tape. Such second sections need only extend for example up to two thirds the height of the pressure pad. Indeed it is not essential for the second sections to lie against entirely the end surfaces of the pressure pad when the pressure pad is in an undeformed state. The second section has a structural function which is to ensure retention of planarity of the elastic tape prior to use of the plaster and only a short section which need not even be at right angles to the first section will suffice to act as the aforementioned second section of the protective strip. The protective strips thus serve as support brackets for the elastic tape. However, once again, it is necessary that deformation of the pad should enable rotation of the second sections to take place into an orientation in which they can be readily gripped by a medical attendant prior to pulling the protective strips from the elastic tape, the latter action taking place after the pad has been applied to the punctures to be covered.

DESCRIPTION OF THE PREFERRED EMBODIMENTS

Figure 1:
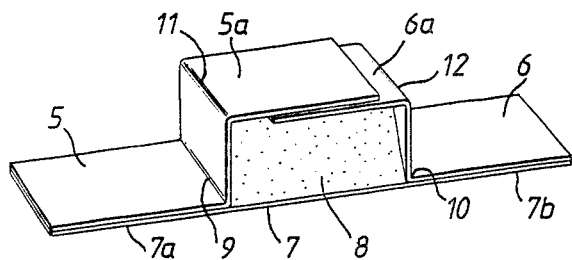
FIG. 1 is a perspective view of a preferred form of surgical plaster embodying the invention.

Referring to the drawings, the surgical plaster of the invention, hereinafter generally termed "the dressing"; is a self-contained unit that both structurally and in its method of application can satisfy all the previously stated requirements for a pressure dressing to be used following venepuncture.

Figure 2:
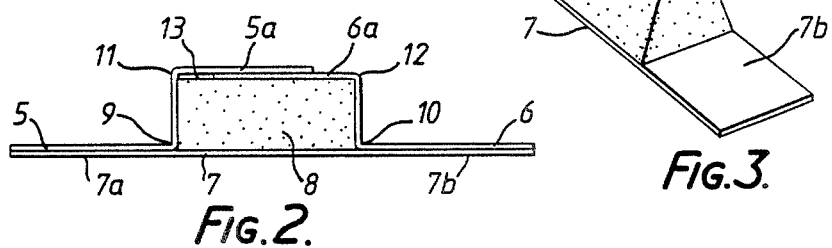
FIG. 2 is a longitudinal section through the plaster of FIG. 1.

FIGS. 1 and 2 show a pressure pad 8 lying centrally on the adhesive surface of a highly elastic adhesive tape 7 which runs the whole length of the dressing and across its width and includes end regions 7a and 7b. Covering strips 5 and 6 are of approximately equal size and in the drawing cover exactly the otherwise exposed surfaces of the adhesive tapes at regions 7a and 7b respectively before being inherently curved or angled through 90° at lines 9 and 10 and 11 and 12 and then running to overlap at regions 5a and 6a compression base area 13 (FIG. 3), regions 5a and 6a each extending approximately 75% of the length of the pressure pad 8. The pad 8 itself is preferably of a spongy and therefore absorbent material and is readily compressible but firm enough to exert pressure on a venepuncture wound site without collapsing under the tension applied to it by the elastic tapes. The material of the pad is suitably a soft foamed plastics so that it is absorbent and compressible. The texture of the foam should be firm enough to produce pressure without collapsing the pad when the highly elastic tape forces it onto the venepuncture site. Preferably when the pad has the preferred dimensions set out hereinafter it should deform when a load of 200 gms is placed as an equally distributed load on the surface 18 (FIG. 4). Too hard a consistency could prove uncomfortable for the patient, and may cause surface 19 (FIG. 5/6) to act as a rigid rather than easily collapsible structure and, on compression at 14 and 15, to move vertically upwards away from surface 13 with faulty flap rotation resulting. The pad should also be capable of being sterilised and be non-irritating and non-allergenic. The synthetic sponge material used in the construction of 'toe separators' has been found to perform very satisfactorily in the preferred embodiment of the invention.

The basic concept of the invention has arisen from consideration of the plant named the "Snapdragon" which is of the genus Antirrhinium and has a bag-shaped flower like a dragon's mouth. When the lateral sides of the base of the flower are squeezed together the 'dragon's mouth' opens.

In much the same manner, when finger tip pressure is applied to the sides of the central pad of the pressure dressing, each lateral protective strip attached to a portion of adhesive elastic tape is caused to rotate laterally, upwards and away from the now exposed wound contact area of the pad. Both strips have previously covered, protected and thus maintained the pad in an aseptic (sterile) state. This mechanical execution is possible due to the designed shape and size of the invention's pad and due to each protective strip being of resilient material and being inherently curved or angled into the perpendicular at the position on the pad where protective strip first meets elastic tape and at the line where vertical end of pad joins the smaller horizontal area of pad base.

Figure 3:
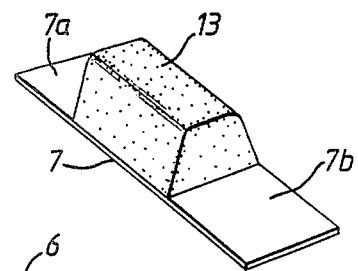
FIG. 3 is a perspective view of a preferred embodiment of pressure pad of the plaster showing attached elastic adhesive tape.
Figure 4:
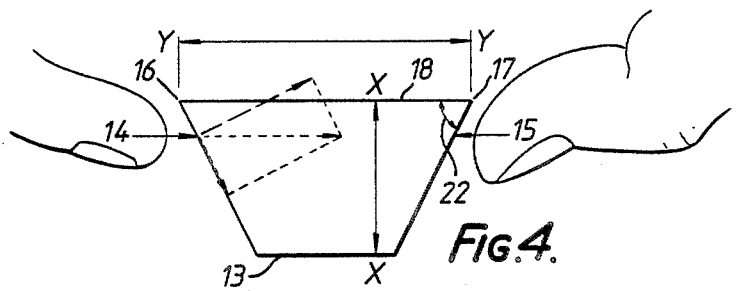
FIG. 4 is a cross-section through the pressure pad of the preferred embodiment illustrating diagrammatically the directions of forces resulting from compression.
Figure 5:
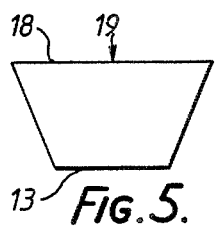
FIG. 5 is a cross-section through the pressure pad of FIG. 4 prior to compression.
Figure 6:
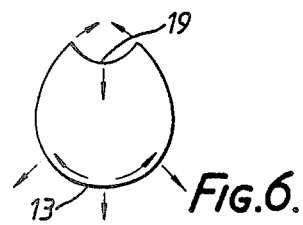
FIG. 6 is a cross-section through the pressure pad of FIG. 4 illustrating the distortion resulting from its compression.

As shown in FIG. 3 the pad in cross-section is a trapezoid whose non-parallel sides are equal, with the larger horizontal surface being fixed longitudinally to the adhesive tape. This shape is desirable for reliable rotation of the protective strips and partially attached adhesive tape and to maintain sterility of surface 13. The pad's areas 16 and 17 (see FIG. 4) present themselves invariably to the grasping tips of thumb and middle finger leaving the lower pad surfaces free from unnecessary contact. When equal pressure is applied at 14 and 15, the predominant resultant force acts in an upward and inward direction. FIGS. 5 and 6 illustrate the shape alteration in the pad and depict the directions in which the pad's bulk tends to move. The bulging of surface 13 in lateral and downward directions enlarges this area for presentation to the puncture site and increases the distance between the compressing digits and itself thus maintaining asepsis.

More particularly, because such a pressure pad is a trapezoid in cross-section whose non-parallel sides are equal and inclined upwardly outwardly from the wound contact areas and towards the elastic tape (see FIG. 4), when the tips of the thumb and middle finger of one hand touch the mid-points of the lateral sides of the pad along its length in order to pick it up, contact only with the upper part of the pad is initially favoured due to its shape. When these finger tips are pressed together the predominant resultant force, as illustrated by the parallelogram in FIG. 4, acts in an upwards and inward direction. This causes the upper larger horizontal and readily compressible surface of the pad covered with adhesive tape to deform into a U shape in cross-section and for an area at point 19 (FIG. 5) to descend towards the wound surface of the pad at 13 (FIG. 6). Thus with increasing digit pressure, not only does the same pad wound surface bulge in a lateral direction, thus presenting a greater area to make contact with the skin over the puncture site, but it bulges in a downwards direction. Thus the digit tips which have contact only with the upper sides of the pad are further removed from the base and its aseptic application area thus enhancing sterile considerations.

This deformation of the pad by digit tip pressure causes the adhesive tape attached to the larger horizontal surface of the pad (FIGS. 1, and 3) to follow the lines of compression. Thus when the identical areas at 16 and 17 (FIG. 4) are compressed by forces 14 and 15 the lateral borders of the tape are obliged to move also upwards and inwards and its central area downwards. As it is also attached to both horizontal surfaces of the protective strips (5 and 6 in FIGS. 1 and 2) and because these strips are both of material stiff enough to be inherently curved or angled along lines 9 and 10, and 11 and 12, the flaps are caused to rotate at lines 9 and 10 (see FIG. 7). The aseptic (sterile) area 13 has thus now become freed of its coverings and can be immediately pressed on to the puncture site. The previously free index finger of the hand holding the dressing can now apply pressure on the pad.

The invention thus has the further advantages of being an aseptic sterile dressing of the same size or smaller than a standard plaster, but also a dressing which the digits of one hand only pick up from a suitable resting place, swing the protective strips away from the wound contact area of its pad's base, and apply at once to the puncture site.

Figure 10:
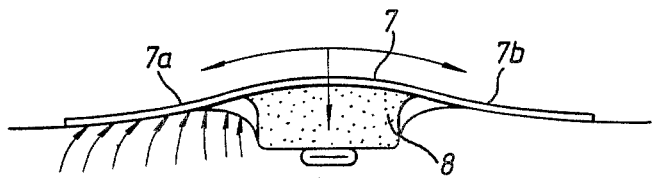
FIG. 10 is a longitudinal section through pad and adhesive tape illustrating lines of force exerted on the former and skin by the tension induced following stretching of the highly elastic tape and application to skin.

With the dressing of this invention, while the index finger of one hand is pressing the pad onto the venepuncture site, the opposite hand removes the needle from the vein. The latter hand peels off the readily presenting ipsilateral strip—5 or 6 in FIG. 7 (by grasping 5a or 6a) and stretches the previously underlying highly elastic adhesive tape until firm resistance is felt and applies it to the skin. The index finger of the same hand assumes pad pressure allowing the other hand now to repeat the process of strip removal and tape application under tension to the skin on the remaining side of the pad. The mobile subcutaneous tissues beneath the skin absorb some of the tension from the tape but, as the latter is highly elastic and tends to return to pre-stretch size, sufficient tension is left within it to pull the centrally attached pad onto the puncture wound and prevent bleeding by efficient wound compression (FIG. 10).

The whole process, from the moment the dressing is picked up until it lies maintaining effective blood vessel compression, and including needle removal, can be accomplished within approximately 8 seconds.

Figure 7:
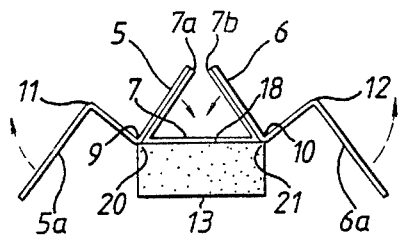
FIG. 7 is a longitudinal section through the plaster of FIG. 2 showing the flap positions reached following their rotation which is induced by pad compression.

In size it is important that the pad 8 should be long enough to allow forces 14 and 15, applied at 16 and 17 (FIG. 4) at the mid-point of these lateral surfaces, to act without contact being made with the axes of rotation along lines 9 and 10 (FIG. 7). Fingers vary greatly in size and the dressing must be problem free for all medical attendants. The length of the pad is preferably at least 2.4 cm, more preferably being 2.5 cm long.

The height of the pad 8 (see line X—X in FIG. 4) is predominantly dependent on the pad's ability to maintain firm pressure when venepuncture is performed in anatomical recesses, including when applied to the cubital fossa at the elbow. Here the height over which the tension within the elastic tape acts is lost to some extent. The pad's ideal height also allows the opposed fingers of one hand to be removed adequately from the pad's wound contact surface thus maintaining the latter's aseptic state. However too great a height is aesthetically undesirable. The pad height is preferably 1.1 cms, although for paediatric use, for example, a pad height of 0.8 cms allows the dressing of the invention to function perfectly adequately provided those attendants with large fingers then take a little more care when grasping the dressing.

The width of the pad (see line Y—Y in FIG. 4) is dependent on the desired amount of flap rotation. The greater this parameter the greater the maximum rotation possible. However aesthetic and practical considerations limit the size. The width of the pad preferably is 2.1 cms. Too small a width however will reduce the area of pad wound surface 13 possible and will also reduce the space between the compressing fingers which the index finger must enter to exert pad compression.

It should be noted that although the preferred dressing embodying the invention is the same length, both in tape and pad size, to a standard plaster, e.g. 'Band-aid', the width of tape and pad is less. This tends to counteract the possible aesthetical disadvantages imposed by the height of its pad.

The optimum inclination (angle 22 in FIG. 4) of side walls which gives the pad its inherent cross-sectional shape of a trapezoid whose non-parallel sides are equal is dependent on the resultant size of the pad wound surface 13 and on the firmness of the pad resulting from the amount of material necessarily cut away in forming the angle. Angle 22 in the preferred embodiment is 27°, but slight variations outside this are permissible, e.g. inclinations to the horizontal of 24–30° are quite feasible.

Figure 11:
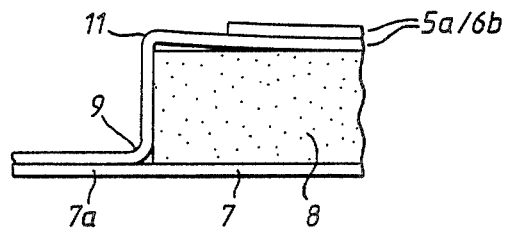
FIG. 11 is a diagrammatic illustration, relating to FIG. 2 of the desirable free area of adhesive tape 7/7a unattached to cover 5a along line 9.

The protective strips (FIGS. 1 and 2) are of approximately equal size and adhere to the adhesive side of the elastic tape. The pad area 13 is thus well protected from septic contamination prior to using the dressing not only by the strips but also by being recessed inwards due to the inward inclination of the pad's long sides. It is highly desirable that attachment of strips to tape at lines 9 and 10 is incomplete so that a small bilateral area of free tape exists (FIGS. 11 and 8), for this will allow maximum flap rotation which might otherwise be limited due to pressure of pad area 19 (FIG. 5) at 20 and 21 (FIG. 7) which will cause the pad area to interfere with the terminal stage of motion of the flaps. The material of the strips is preferably such that they are resilient but firm enough not only to support the adhesive tape in a horizontal plane so that a maximum degree of rotation is possible but also to maintain the set curves or anglings at lines 9 and 10, and 11 and 12, in a satisfactory fashion. It is therefore undesirable that the resilience should be less than that found in plain white 85 gm/cm$^2$ typing paper.

The highly elastic adhesive tape of the dressing runs the whole length thereof. It is ideally transparent and may be perforated. It should be strong enough to allow it to be stretched lengthwise and applied under tension without breaking. Preferably it should be stretchable by 50% of its original length and able to return to its original size when tension is released. An unstretched length of 7.5 cms, in common with standard plasters is preferred. Its width is preferably that of the pressure pad at surface 18 (FIG. 4), i.e. preferably being 2.1 cms. The adhesive qualities, i.e. tackiness of the adhesive coating on the tape should allow it to adhere firmly to the skin but permit the protective strips to be peeled off easily without adhesive being deposited on them. A perforated plasticised, polymer film, preferably clear PVC film coated with a pressure-sensitive acrylic adhesive, such as used in the manufacture of "Steripad" postoperative dressings, has been found to be suitable. However, both cast and calendered PVC films will give equivalent performance. Any pressure-sensitive adhesive, e.g. solvent acrylic, emulsion acrylic, or a hot-melt adhesive can be used. The perforations can also be formed in different ways, e.g. by using hot pins or punching. Other film-forming plastics materials which can be used to form the tape include modified polyethylenes, such as EVA or EMA both of which are transparent and flexible though less easy to coat with adhesive, and a polyurethane film which suffers less from the latter disadvantage.

Figure 8:
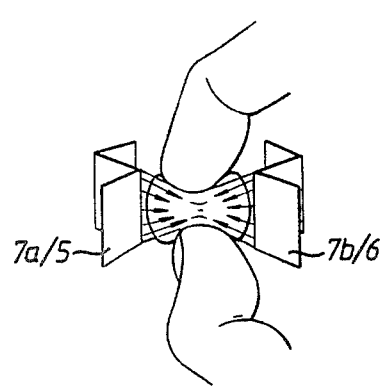
FIG. 8 shows the plaster viewed from above illustrating the directions of the transitional forces imposed upon the elastic tape and the adherent covers resulting from pad compression.
Figure 9:
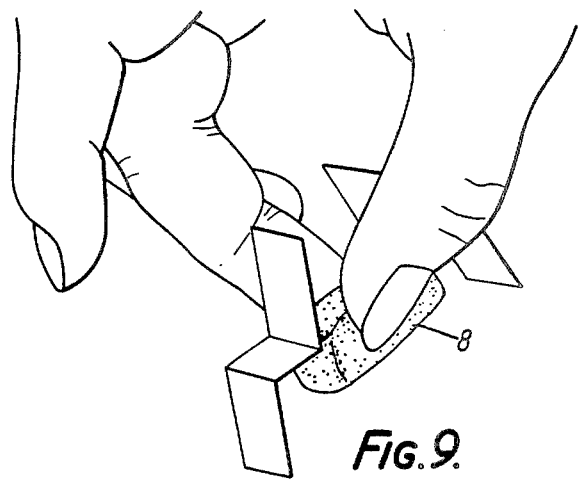
FIG. 9 is a diagram illustrating availability of free index finger for pad pressure by insertion between thumb and middle finger, these latter two digits having caused flap rotation (as in FIG. 7) by pad compression.

FIG. 8 shows the dressing immediately prior to application, with the protective strips and partially attached elastic tape rotated away from the pad base due to pad compression between thumb and middle finger. This allows the free index finger (seen as such in diagram) to come between these two fingers and apply pressure on the pad (surface 18) when the latter is placed directly over the venepuncture site.

Before application of the plaster is is important that the skin should be dry and clean and therefore free of moisture, powders or grease which would otherwise interfere with satisfactory tape adherence.

The application of the plaster, including removal of the needle, is completed in approximately 8 seconds. This time can be reduced when experience in handling the dressing is achieved.

Figure 12:
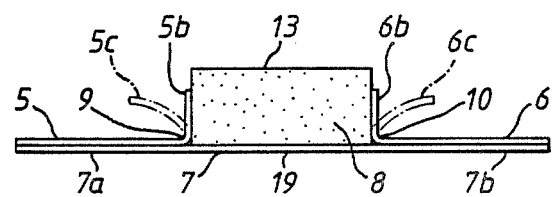
FIG. 12 is a longitudinal section through an alternative form of surgical plaster embodying the invention.

Reduced performance while nevertheless enabling the object of the present invention to be achieved is attained with the dressing shown in FIG. 12 of the accompanying drawings. The dressing differs from that shown in FIGS. 1 and 2 in two fundamental respects. Firstly, the pad 8 is a rectangular block and secondly, the covering strips 5 and 6, first sections of adhere to end sections 7a and 7b respectively of adhesive tape 7, terminate in second sections 5b and 6b respectively lying against vertical end faces of the rectangular pad at a height about two thirds of the way up the pad to avoid compression of strips between pad and skin. This means that the covering strips do not provide a sterile covering for the surface 13 of the pad. The sterile covering will be provided in practice by the packaging with which the dressing is associated. A suitable form of packaging will be described hereinafter. Moreover, shown in dotted lines in FIG. 12 is an alternative form of second section of the covering strips which acknowledges the fact that the stiffness of the covering strips is not critical per se. Rather, the strips, through their inherent angling or curvature are to provide a combination hinge/support bracket function with respect to first sections of the covering strips and the adhesive tape. After a short transition section adjacent lines 9 and 10, sufficient to ensure that the covering strips act as support brackets for the adhesive tape, the covering strip curves away from the end surfaces of the pad 8 in tabs 5c and 6c. Curvature is shown somewhat exaggeratedly in FIG. 12. The tabs 5c, 6c, like the sections 5b, 6b will need to rotate before they can be readily gripped on application of the dressing to a wound and pulled clear from the adhesive strip. This is achieved according to the snapdragon principle already discussed.

In contrast to the use of a trapezoidal pressure pad, when this pad is rectangular in cross-section, then when the dressing is held horizontally with adhesive tape uppermost, compression forces applied exactly laterally to the pad will act at right angles to the vertical and the forces exerted will act upon the pressure pad to deform it opposite to the manner shown in FIG. 6. However, if the natural tendency to grasp the upper lateral surfaces of the pad is realised or the digits move as through squeezing a grasped pip away from them, then this will cause much the same pad deformation as in FIG. 6 and rotation of the protective strips to enable the object of the invention to be attained.

Figure 13:
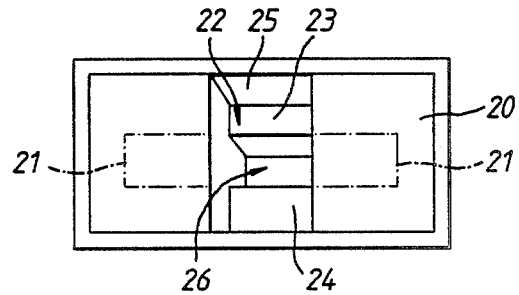
FIG. 13 is a perspective view of a container for housing the plaster of FIG. 12 in a sterile condition prior to use.

Turning next to FIG. 13, a suitable form of dispenser for the dressings of the invention is shown. This form of dispenser is of particular value in connection with the embodiment of FIG. 12, although it can also be employed with any form of dressing embodying this invention. The dispenser is either as shown in FIG. 13 or is constituted by a plurality of sections of like form to the dispenser shown in FIG. 13 lying adjacent to each other in a line or in an array forming, in effect, a tray. A plurality of such trays may be stacked in a container. The individual dispenser as such or as part of a tray comprises an upper section 20 for receiving the dressing with the non-adhesive side of the adhesive tape uppermost. The position of the ends of the tape is shown in broken lines at 21. A central section 22 of the dispenser is shaped to receive the adhesive pad with the covering strips thereover. In the middle, the central section has a depth equal or slightly in excess to the height of the pad. At the flanks there are shelves 23 and 24 at the level approximately of the mid-height of the pad. The intention here is that between the pad and the wall 25 of the dispenser there will be a space within which finger and thumb can be inserted to lift the dressing out of the dispenser. The dispenser will have been manufactured under sterile conditions and the opposite surface of the pad to that adhering to the adhesive tape will have remained in contact with a sterile surface 26 at all times. Thus once the dressing has been lifted from the dispenser by positioning finger and thumb in the finger spaces to the side of the pad to contact upper lateral surface regions thereof, the pad can be placed over a puncture hole without adjusting the position of finger and thumb, thereby keeping sterile the surface of the pad previously in contact with the base of the dispenser. Only then, without changing position of finger and thumb, will pressure be applied to cause rotation of portions 5b, 6b (or 5c, 6c) of the covering strips into an orientation in which they can readily be pulled off before the adhesive tape is applied to the skin. Alternatively, it may be expedient to apply to the top surface of the pad the pressure of a single finger, the finger that presses the pad onto the puncture site.

The rotation according to the snapdragon principle which is then achieved is however a compromise compared to that which can be achieved with the trapezoidal form of pad and does not detract from the considerable advantages gained as previously described when the trapezoidal pad is present.

With the embodiment of FIG. 12, it is to be noted that preferred dimensions, especially height, width and length of pad and preferred materials of the pad and the covering strips are as already discussed in connection with the embodiment of FIGS. 1 and 2.

I claim:

1. A surgical plaster comprising:
   (a) a length of elastic tape having a tacky surface;
   (b) a resilient pressure pad having a pair of opposed transverse surface regions and a pair of opposed lengthwise surface regions the pad being attached to the tacky surface of the elastic tape proximate a central region thereof so as to define a pair of end regions on the tape separated by the pad;
   (c) a pair of removable protective strips adhered along a first section thereof to respective end regions of the tacky surface of the elastic tape and including a second section which extends at an angle to said first section away from the tacky surface at the tape, wherein the first sections of the strips extend to respective surface regions of the pad which extend substantially transversely to the tacky surface of the tape; and
   (d) a means connected to the second section of each of the strips which covers that surface of the pad opposite the surface of the pad coupled to the tape;
   (e) wherein (i) the strips have sufficient stiffness to provide an inherent set curvature or angling of the form of the strips, (ii) the second section has a sufficient length effective to support the first section and thereby maintain the tape in a substantially flat configuration when held adhesive tape uppermost, and (iii) the pad has sufficient resilience such that when the pad is manually compressed at the surfaces extending substantially lengthwise of the tape, the curvature or angling of the strips is altered so as to rotate the second sections of the strips and increase the angle between the second sections of the strips and the surface regions of the pad extending transversely of the tape.

2. A surgical plaster according to claim 1 in which the pressure pad is formed of a soft foam synthetic plastics material.

3. A surgical plaster according to claim 2 in which the pressure pad is formed of a foam which when dimensioned to be 0.8 cm high, 2.4 cm long and having a maximum width of 2 cm, begins to deform when a load of 200 grams is uniformly distributed on the surface which the defined plaster adheres to the elastic tape.

4. A surgical plaster as claimed in claim 1 wherein the pressure pad is a trapezoidal transverse cross-section with its non-parallel sides being equal and extending lengthwise of the tape, the surface lying on the tape being larger than the opposite surface.

5. A surgical plaster as claimed in claim 4, wherein said non-parallel sides of the pad are inclined to the pad surface lying on the tape at 24–30°.

6. A surgical plaster as claimed in claim 4, in which the pressure pad is formed of a foam which when dimensioned to be 0.8 cm high, 2.4 cm long and having a maximum width of 2 cm, begins to deform when a load of 200 grams is uniformly distributed on the surface which the defined plaster adheres to the elastic tape.

7. A surgical plaster as claimed in claim 6, wherein said non-parallel sides of the pad are inclined to the pad surface lying on the tape at 24–30°.

8. A surgical plaster as claimed in claim 4, wherein the second section of each said protective strip is of such length that it has undergone angling of its form into a portion overlying the pad surface opposite that lying on the tape, and providing said means covering and maintaining sterile said opposite surface of the pad, the portion of one strip lying over said opposite surface of the pad overlapping the portion of the other strip lying over said opposite pad surface.

9. A surgical plaster as claimed in claim 8, wherein the overlapping of strip portions occupies at least 75% of the length of said opposite surface of the pad.

10. A surgical plaster as claimed in claim 9, wherein said non-parallel sides of the pad are inclined to the pad surface lying on the tape at 24–30°.

11. A surgical plaster comprising:
an elastic tape one surface of which is tacky, a resilient sterile pressure pad adhering to the tacky surface of the elastic tape in a central region thereof which pad is of trapezoidal transverse cross-section with its non-parallel sides being equal and extending lengthwise of the tape, the surface lying on the tape being larger than the opposite surface;
a pair of removable protective strips adhering at first sections to respective end regions of the tacky surface of the elastic tape and extending up to surface regions of said pad extending transversely of the tape, the strips each being of material stiff enough to ensure the inherent set angling of its form into a second section at an angle to said first section overlying the tape, said second sections being of such length that they have undergone angling of their form into portions of each overlying the pad surface opposite that lying on the tape and overlapping to cover and maintain sterile the surface of the pad opposite that lying on the tape prior to removal of said strips from the tape;
the resilience of said pad being such that manual compression of the pad at surfaces extending lengthwise of the tape deforms the pad to an extent sufficient to alter said curvature or angling of the strips and rotate said second sections so as to increase the angles between them and the surface regions of the pad extending transversely of the tape.

12. A surgical plaster as claimed in claim 11, wherein the pressure pad is formed of a foam which when dimensioned to be 0.8 cm high, 2.4 cm long and having a maximum width of 2 cm, begins to deform when a load of 200 grams is uniformly distributed on the surface which the defined plaster adheres to the elastic tape.

13. A surgical plaster as claimed in claim 11, wherein said non-parallel sides of the pad are inclined to the pad surface lying on the tape at 24–30°.

14. A surgical plaster as claimed in claim 11, wherein the overlapping of strip portions occupies at least 75% of the length of said opposite surfaces of the pad.

15. A surgical plaster comprising:
an elastic tape one surface of which is tacky;
a resilient sterile pressure pad adhering to the tacky surface of the elastic tape in a central region thereof;
a pair of removable protective strips adhering at first sections to respective end regions of the tacky surface of the elastic tape and extending up to surface regions of said pad extending transversely of the tape, the strips each being of material stiff enough to ensure set curvature or angling of its form into a second section at an angle to said first section overlying the tape, said second sections of the protective strips extending to a position short of a level beyond said opposite surface of the pad; and
a dispenser covering and maintaining sterile the said opposite surface of the pad is constituted by a dispenser for the plaster, which dispenser provides a flat surface supporting the elastic tape and contacted by said first sections of the protective strips, which flat surface is interrupted by a box-shaped cavity occupied by the pressure pad, the interior of which cavity has been provided in a sterile condition;
the resilience of said pad being such that manual compression of the pad at surfaces extending lengthwise of the tape deforms the pad to an extent sufficient to alter said curvature or angling of the strips and rotate said second sections so as to increase the angles between them and the surface regions of the pad extending transversely of the tape.

16. A surgical plaster as claimed in claim 15, wherein said cavity has a width greater than the width of the elastic tape and incorporates, at a position alongside each longitudinally extending surface of the pressure pad to be gripped in withdrawing the plaster from the dispenser, an intermediate ledge restricting the transverse cross-sectional area of the cavity substantially to the transverse cross-sectional area of the pressure pad adjacent the ledge.

17. A surgical plaster as claimed in claim 15, wherein the second sections of the protective strips possess a length not exceeding two thirds the height of the pressure pad.

18. A surgical plaster as claimed in claims 15, wherein the shape of the pressure pad is that of a rectangular block.

19. A surgical plaster as claimed in claim 16, wherein the shape of the pressure pad is that of a rectangular block.

* * * * *